United States Patent [19]

Harris et al.

[11] Patent Number: 5,391,157
[45] Date of Patent: Feb. 21, 1995

[54] END OF DOSE INDICATOR

[75] Inventors: Dale C. Harris, Fairland, Ind.; John S. Ploof, Mundelein, Ill.

[73] Assignee: Eli Lilly and Company, Indianapolis, Ind.

[21] Appl. No.: 963,801

[22] Filed: Oct. 20, 1992

[51] Int. Cl.⁶ .............................................. A61M 5/00
[52] U.S. Cl. ..................... 604/208; 604/210
[58] Field of Search ..................... 604/65–66, 604/100, 118, 207–208, 186, 189, 169, 210–211, 260, 409, 28, 232; 221/2, 3; 222/23, 39, 41, 46, 402.13

[56] References Cited

U.S. PATENT DOCUMENTS

| | | |
|---|---|---|
| 2,823,675 | 2/1958 | Sciurba . |
| 3,002,517 | 10/1961 | Pitton ................................ 401/172 |
| 3,232,117 | 2/1966 | Gilmont . |
| 3,613,952 | 10/1971 | Gilmont ............................... 222/43 |
| 3,815,785 | 6/1974 | Gilmont ............................... 222/46 |
| 3,884,230 | 5/1975 | Wulff . |
| 4,096,751 | 6/1978 | Withers et al. ..................... 734/425.6 |
| 4,275,729 | 6/1981 | Silver et al. ........................ 604/211 |
| 4,340,051 | 7/1982 | Leibinsohn . |
| 4,344,573 | 8/1982 | De Felice . |
| 4,367,739 | 1/1983 | Le Veen et al. . |
| 4,395,921 | 8/1983 | Oppenlander ..................... 73/864.1 |
| 4,413,760 | 11/1983 | Paton ................................ 222/309 |
| 4,475,905 | 10/1984 | Himmelstrup ..................... 604/208 |
| 4,498,904 | 2/1985 | Turner et al. ...................... 604/211 |
| 4,592,745 | 6/1986 | Rex et al. ........................... 604/211 |
| 4,710,179 | 12/1987 | Haber et al. ....................... 604/211 |
| 4,810,249 | 3/1989 | Haber et al. ....................... 604/210 |
| 4,865,591 | 9/1989 | Sams ................................. 604/186 |
| 4,883,472 | 11/1989 | Michel .............................. 604/208 |
| 4,936,833 | 6/1990 | Sams ................................. 604/232 |
| 4,973,318 | 11/1990 | Holm et al. ........................ 604/208 |
| 5,092,842 | 3/1992 | Bechtold et al. ................... 604/135 |
| 5,112,317 | 5/1992 | Michel .............................. 604/208 |
| 5,114,406 | 5/1992 | Gabriel et al. ..................... 604/136 |
| 5,158,206 | 10/1992 | Kobayashi et al. ................. 222/39 |

FOREIGN PATENT DOCUMENTS

| | | |
|---|---|---|
| 0000465 | 1/1979 | European Pat. Off. ............ 604/207 |
| 268191 | 5/1988 | European Pat. Off. . |
| 327910 | 8/1989 | . |
| 338806 | 10/1989 | European Pat. Off. . |
| 450905 | 10/1991 | European Pat. Off. . |
| 496141 | 7/1992 | European Pat. Off. . |
| 250467 | 10/1987 | German Dem. Rep. . |
| 1632032 | 11/1977 | Germany . |
| 3031830 | 3/1983 | Germany . |
| 8804656.7 | 9/1988 | Germany . |
| WO 87/02895 | 5/1987 | WIPO . |
| WO 88/07874 | 10/1988 | WIPO . |
| WO 91/02557 | 3/1991 | WIPO ....................... A61M 5/315 |

*Primary Examiner*—C. Fred Rosenbaum
*Assistant Examiner*—V. Alexander
*Attorney, Agent, or Firm*—Douglas J. Taylor; Leroy Whitaker

[57] ABSTRACT

The present invention provides an improvement in injection syringes by providing for an end of dose indicator which is operatively associated with the dose knob of an injection syringe. The instant end of dose indicator works by providing a sound as an indication that the complete dose has been administered.

5 Claims, 1 Drawing Sheet

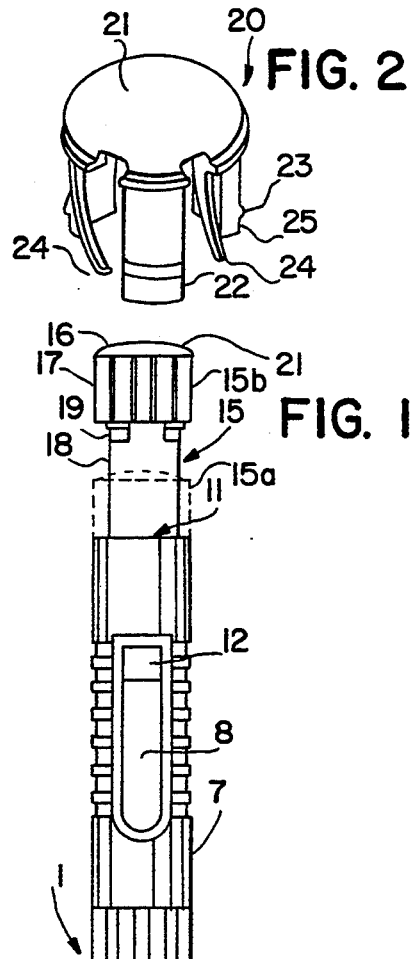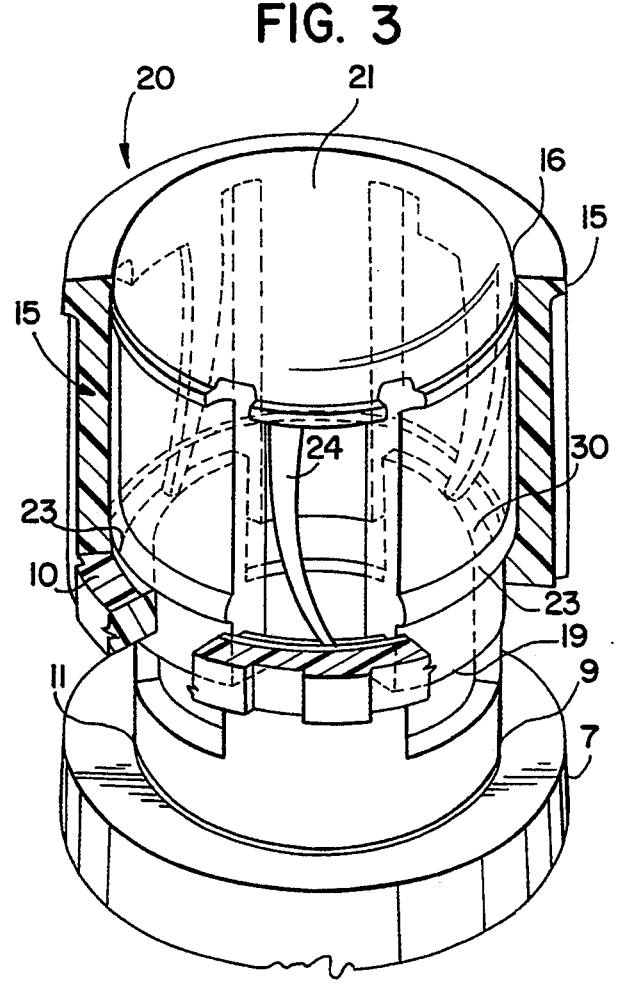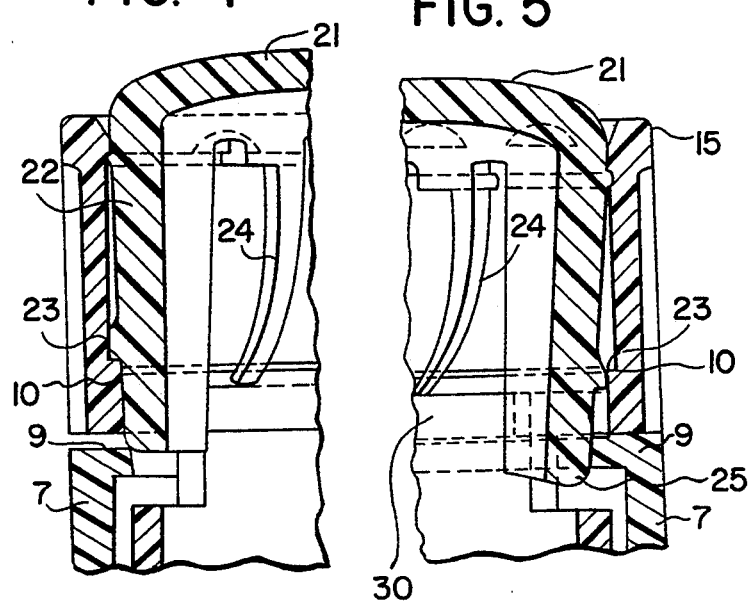

5,391,157

1

END OF DOSE INDICATOR

BACKGROUND OF THE INVENTION

1. Field of the Invention

This invention is in the field of devices for injecting precisely metered doses of pharmaceutical agents. The invention particularly relates to a hypodermic syringe having the same general appearance as a pen or mechanical pencil which is specifically adapted to provide for multiple measured doses of agents such as insulin or human growth hormone.

2. Description of the Prior Art

Diabetics and others frequently fine themselves in situations where the assistance of a health professional is unavailable to administer a subcutaneous or intramuscular injection of measured amount of a liquid agent. In such situations such persons need to have a low cost syringe which does not require the assistance of a health professional to achieve the desired measure of accuracy. It is often the case that such persons require more than one dose per day, each dose being of a somewhat different volume. Dispensers of this general type are known which are the general appearance of a pen or mechanical pencil. The dispenser is typically large enough to hold several such doses, yet it is small enough to fit conveniently in one's pocket or purse. Examples of such devices are to be found in U.S. Pat. Nos. 4,973,318; 4,413,760; 4,498,904; 3,613,952; 4,475,905; 4,883,472; and 4,592,745. Additional examples are show in PCT International Publications WO 87/02895; WO 88/07874; WO 82/02662; PCT CH 86/00151; PCT DK 88/0064.

In devices of this class, a container of the liquid is generally provided having a closed first end adapted to be penetrated by a needle assembly so as to permit the liquid in the container to pass out the injection. The second end of the container is generally closed by a piston. To prevent tampering or reuse of the liquid container, the piston is generally designed such that a pushing force can be applied to the piston to reduce the liquid-holding volume of the container, but no feature is presented which would be suitable for pulling on the piston so as to enlarge the liquid-holding volume of the container.

An elongated member in the nature of a plunger rod is received within the housing for exerting a force on the piston closing the second end of the container. A means is provided for measuring the distance which the plunger rod travels to determine the decrease in volume of the liquid container which causes the dispensing of the liquid within the container. It has generally been recognized that the dispenser should have some feature which would allow the rod to only travel in a single direction toward the piston thereby preventing any action on the part of the rod which might permit an enlargement of the volume of the liquid container. A safety cover is generally provided over a needle assembly attached to the closed end of the container.

While the prior art pen-style syringes have met with some success, certain shortcomings have also been observed. In some prior art pens it is difficult to be sure the entire intended dose has been administered. The device of this invention assures that the complete dose is administered by providing a clicking sound when the dose is completed.

2

SUMMARY OF THE INVENTION

The device of this invention provides an improvement in injection syringes by providing for a sound as an indication that the complete dose has been administered. Essentially, the improvement is a molded imitator which fits into or is operatively associated with a dose knob of a syringe assembly.

The end of dose indicator of this invention is operatively associated with the dose knob of a hypodermic syringe which is raised to set the dose and pushed to inject the dose. The end of dose indicator comprises a means for producing a sound which is set to produce a sound when the dose knob is pushed to the end of the dose and a means for resetting the means for producing a sound when pressure is released from the dose knob after the dose is injected.

The indicator has top section with resilient legs depending perpendicularly from the top section. The outer surface of the resilient legs has a ridge which rests on a ledge inside the base of the dose knob. The indicator has resilient curved legs which rest on another ridge inside of the dose knob. The dose knob has an elongated section which fits into a cylindrical sleeve such that when the dose knob is pushed into the sleeve, at the end of the injection, the top portion of the sleeve touches end of the leg of the resilient legs displacing the ridge from the ledge and causing a snapping noise. The resilient curved legs cause the ridge to reassume its position on the ledge when pressure is released from the top of the indicator.

Thus, as the top of the indicator is pushed there will be a snapping noise at the end of the dose and when pressure is released from the top of the indicator the indicator is reset through the resilient spring legs. In its simplest form the invention encompasses an indicator with a top having resilient legs with means for releasable positioning the resilient legs in a predetermined position in the dose knob, means for releasing the resilient legs from the predetermined position at the end of the dose, and a resilient means for returning the resilient legs to the predetermined position.

BRIEF DESCRIPTION OF THE DRAWINGS

FIG. 1 is a top perspective view of an insulin pen.

FIG. 2 is a elevated perspective view of end of dose indicator.

FIG. 3 is a sectional view of the end of dose indicator cooperating with the dose knob.

FIG. 4 is a vertical cross-section of FIG. 3 showing the indicator is the set position.

FIG. 5 is the same vertical cross-section view of FIG. 4, showing the position of the resilient leg after the release and snap.

DETAILED DESCRIPTION OF THE INVENTION

One embodiment of the end of dose indicator is an integrally molded piece adapted to fit in and cooperate with the dose knob. Such an embodiment comprises a top section with resilient legs perpendicularly dependent from the top section and having a means, usually a ridge on the outer surface of the resilient legs, for retaining the resilient legs in a predetermined postion in the dose knob until the end of the dose is reached. At the end of the dose the resilient legs are released from the predetermined position causing a snapping noir. The end of dose indicator also has a means for returning the resilient legs to their predetermined position. This function can be accomplished by curved legs also perpendicularly depending from the top section of the end of dose indicator and bend in the plane of the curve which is tangential to the circular top section. Such legs cooperate with the inner surface of the dose knob by resting on a ledge. The curved legs are bent when the top section is pushed to deliver the dose and restored to their original position when the pressure is released from the top section and this rest,oration resets the resilient legs to their set position.

Those skilled in this art will recognize large variety of cooperative structures and such as ledges, detents and legs of various number, size, shape, position and material which will serve as alternate means for accomplishing the function of producing a sound at the end of the dose and resilient means for resetting the means for producing the sound.

DESCRIPTION OF THE PREFERRED EMBODIMENT

The syringe assembly 1 is shown in FIG. 1. The syringe assembly 1 includes a needle assembly 2 which is coupled at the distal end of a syringe 3 which holds within it a container 4 containing the liquid to be administered. A threaded piston rod 5 contacts plunger 6 such that the piston 5 moves plunger 6 and downward movement forces liquid out of the needle. Overcap 7 is slidably received by the proximal end of the syringe housing 3. A pocket clip 8 is integrally molded as a part of overcap 7. A dose knob 15 fits into an opening 11 at the proximal end of the overcap 7. Rotating dose knob 15 cause an internal nut coupled to the dose knob to ride-up piston 5 and effectively elongates a piston so that the dose knob occupies position 15b which corresponds to a precisely metered dose which can be observed on a scale through window 12. Pushing the dose knob from position 15b to position 15a causes a precisely metered amount of liquid to be ejected through the needle.

The precise description of devices of FIG. 1 as generally explained above is set out in U.S. Ser. No. 07/361,132, filed Jun. 5, 1989, assigned to the same assignee as this application, the specification of which is incorporated herein by reference. Published European Patent Application No. 496,141, published Jul. 29, 1992 is likewise incorporated herein by reference.

The improvement of the present invention is set-out in detail in FIGS. 2, 3, 4 and 5.

FIG. 2 shows an integrally molded end of dose indicator 213. The dose indicator 20 has a top section 21, perpendicular resilient legs 22 with an outer ridge 23 and perpendicular curved legs 24. The dose indicator 20 fits into opening 11 at the top of the dose knob 15 as shown in detail in FIG. 3.

Now considering the cooperation between the dose indicator 20 and the dose knob 15 shown in FIG. 3, the dose knob 15 has a fluted portion 17 and elongated cylindrical section 18 which is smaller is radius than the fluted portion 17 and fits into opening 11. At the base of the fluted portion where 17 joins 18 are openings 19 which expose the bottom portion 25 of resilient leg 22 to proximal end of overcap 7 and a small inward rim 9. Also within dose knob 15 is ledge 113 upon which ridge 23 rests. There is also a ledge 30 on which curved legs 24 rests.

In the embodiment illustrated in FIG. 2 is an integrally molded top with three equally spaced apart resilient legs 22. These resilient legs have a curved surface and resiliently bend inward. Disposed between each of the resilient legs is a curved leg which bends in the direction of the curve. The shorter curved legs rest on ledge segments 30 and the longer resilient legs rest on ledge 10.

FIG. 4 shows the end of dose indicator in a cocked position with curved leg 24 resting on ledge 30 and ridge 23 resting on ledge 10. In the position shown in FIG. 4 the dose knob 15 has been rotated to set a dose. FIG. 5 illustrates what occurs at the end of a dose when the top 21 of the dose indicator 20 is pushed toward rim 9 of overcap 7. The engagement of rim 7 with end portion 25 of resilient leg 23 causes ridge 23 to suddenly dislodge from ledge 10 causing a snapping noise indicating the end of the dose. As the top 21 of the end of dose indicator is pushed curved leg 24 flexes due to pressure against ledge 30. Releasing pressure on 21 causes curved leg 24 to regain its original position shown in FIG. 4 and resets ridge 23 on ledge 10. As can be seen in FIGS. 4 and 5 the resilient leg 22 bends toward the center of the dose indicator 20 whereas curved leg 24 bends in the plane of the curve. During the application of pressure to the top 21 of dose indicator 20 the top deforms in response to the pressure and regains its original position when pressure is released.

Referring again to FIG. 1 for the general operation of the device, dose knob 15 is turned to position 15b to set the proper dose which is observed on a scale through window 12. The needle is injected into the skin and the top 21 of the dose indicator is pressed downward until the dose knob is in position 15a which is indicated by a clicking sound resulting from ridge 23 sliding off of ledge 10. When the pressure is released from 21, curved legs 24 reset ridge 23 on ledge 10. The user is assured of having administered the complete intended dose at the click.

The above examples illustrate the present invention, but do not limit it in spirit or scope.

What is claimed is:

1. An injection syringe having a dose knob and an end of dose indicator which is adapted to fit into said dose knob, wherein said end of dose indicator comprises:
   a) top section
   b) resilient legs perpendicularly dependent from the top section wherein the resilient legs have a means for cooperating with and retaining the resilient legs in a predetermined position in the dose knob as pressure is applied to the top section until the end of the dose and at the end of the dose are released from the predetermined position causing a sound;
   c) means for returning the resilient legs to the predetermined position in the dose knob when pressure is released from the top section.

2. The syringe of claim 1 wherein the means for returning the resilient legs to the predetermined position is one or more curved legs which depend perpendicularly from the top section of the end of dose indicator and cooperate with the dose knob to return the resilient legs to the predetermined position when the dose is completed and pressure is removed from the top section.

3. The syringe of claim 2 where there are three equally spaced resilient legs with a curved leg in the space between the resilient legs.

4. The syringe of claim 3 wherein the resilient legs have a ridge on the outer surface which cooperates with a ledge within the dose knob to retain the resilient legs in the predetermined position until the end of the dose when the ridge is dislodged from the ledge to cause a sound.

5. The syringe of claim 4 wherein the curved legs cooperate with a second ridge within the dose knob to return the resilient legs to the predetermined position when the pressure is released from the top section after the dose is injected.

* * * * *

UNITED STATES PATENT AND TRADEMARK OFFICE
CERTIFICATE OF CORRECTION

PATENT NO.  : 5,391,157
DATED       : February 21, 1995
INVENTOR(S) : Dale C. Harris et al.

It is certified that error appears in the above-indentified patent and that said Letters Patent is hereby corrected as shown below:

Column 3, line 10, "rest,oration" should read, -- restoration --.

Column 3, line 50, "213" should read, -- 20 --.

Column 3, line 63, "ledge 113 upon" should read, -- ledge 10 upon --.

Signed and Sealed this

Twenty-first Day of May, 1996

Attest:

BRUCE LEHMAN

Attesting Officer           Commissioner of Patents and Trademarks